US00PP12528P2

(12) United States Plant Patent
Bergman

(10) Patent No.: US PP12,528 P2
(45) Date of Patent: Apr. 9, 2002

(54) CHRYSANTHEMUM PLANT NAMED 'FROSTED YOELMIRA'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/594,758

(22) Filed: Jun. 16, 2000

(51) Int. Cl.[7] ..... A01H 5/00

(52) U.S. Cl. ..... Plt./287

(58) Field of Search ..... Plt./287, 288, 291

(56) References Cited

PUBLICATIONS

UPOV–ROM, 2001/03, Plant Variety Database, GTI Jouve Retrieval Software, citation for 'Frosted Yoelmira'.*

* cited by examiner

*Primary Examiner*—Howard J. Locker
(74) *Attorney, Agent, or Firm*—C. A. Whealey

(57) ABSTRACT

A distinct cultivar of Chrysanthemum plant named 'Frosted Yoelmira', characterized by its compact, upright, somewhat outwardly spreading and uniformly mounded plant habit; excellent plant strength; small, durable, glossy, dark green leaves; very freely branching habit; uniform flowering response; early flowering, eight-week response time; floriferousness; small decorative-type inflorescences that are about 3.1 cm in diameter; white-colored ray florets with purple-tipped apices; and good postproduction longevity with inflorescences maintaining good substance and color for at least three weeks in an interior environment.

1 Drawing Sheet

BACKGROUND OF THE INVENTION

The present Invention relates to a new and distinct cultivar of Chrysanthemum plant, botanically known as *Dendranthema grandiflora* and hereinafter referred to by the cultivar name Frosted Yoelmira.

The new Chrysanthemum is a product of a mutation induction breeding program conducted by the Inventor in Fort Myers, Fla. The objective of the program is to create new Chrysanthemum cultivars with desirable inflorescence form and floret colors and good postproduction longevity.

The new Chrysanthemum originated by exposing unrooted cuttings of a proprietary seedling selection identified as YB-5908, to X-ray radiation in July, 1997, in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Fort Myers, Fla. The new Chrysanthemum was discovered and selected by the Inventor as a single flowering plant within this population in March, 1998. The selection of this plant was based on its desirable inflorescence form and ray floret color.

Asexual reproduction of the new Chrysanthemum by vegetative tip cuttings was first conducted in Fort Myers, Fla. in May, 1998. Asexual reproduction by cuttings has shown that the unique features of this new Chrysanthemum are stable and reproduced true to type in successive generations.

SUMMARY OF THE INVENTION

The cultivar Frosted Yoelmira has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Frosted Yoelmira'. These characteristics in combination distinguish 'Frosted Yoelmira' as a new and distinct Chrysanthemum:

1. Compact, upright, somewhat outwardly spreading and uniformly mounded plant habit.
2. Small, durable, glossy, dark green leaves.
3. Very freely branching, dense and full plants.
4. Excellent plant strength.
5. Uniform flowering response.
6. Early flowering, eight-week response time.
7. Very freely flowering.
8. Small decorative-type inflorescences that are about 3.1 cm in diameter.
9. White-colored ray florets with purple-tipped apices.
10. Can be grown as a natural spray-type.
11. Good postproduction longevity with inflorescences maintaining good substance and color for at least three weeks in an interior environment.

Plants of the new Chrysanthemum differ from the parent selection and the Chrysanthemum cultivars Yoelmira (U.S. Plant patent application Ser. No. 09/594,757) and Yellow Yoelmira (U.S. Plant patent application Ser. No. 09/594,759 both filed concurrently with this application) primarily in ray floret color.

Plants of the new Chrysanthemum differ from plants of the Chrysanthemum cultivar Surf, disclosed in U.S. Plant Pat. No. 4,585, in the following characteristics:

1. Plants of the new Chrysanthemum are more freely branching than plants of the cultivar Surf.
2. Plants of the new Chrysanthemum have smaller leaves and inflorescences than plants of the cultivar Surf.

3. Plants of the new Chrysanthemum are more floriferous than plants of the cultivar Surf.
4. Ray floret color of the new Chrysanthemum is white with purple-tipped apices whereas ray floret color of plants of the cultivar Surf is completely white.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which more accurately describe the actual colors of the new Chrysanthemum.

The photograph at the top of the sheet comprises a top perspective view of a typical flowering plant of 'Frosted Yoelmira'.

The photograph at the bottom of the sheet comprises a close-up view of typical inflorescences of the cultivar Frosted Yoelmira.

DETAILED BOTANICAL DESCRIPTION

In the following description, color references are made to The Royal Horticultural Society Colour Chart except where general terms of ordinary dictionary significance are used. The following observations and measurements describe plants grown and flowered during the Spring in Salinas, Calif. and Leamington, Ontario, Canada, under greenhouse conditions which approximate those generally used in commercial potted Chrysanthemum production. Four unrooted cuttings were directly stuck in a 15-cm container and pinched once. Plants used for this description were grown as spray-types. Measurements and numerical values represent averages of typical flowering plants.

Botanical classification: *Dendranthema grandiflora* cultivar Frosted Yoelmira.

Commercial classification: Decorative-type potted Chrysanthemum.

Parentage: Induced mutation of proprietary Chrysanthemum seedling selection identified as YB-5908.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous decorative-type potted Chrysanthemum which can be grown as a natural spray-type. Compact; inverted triangle; stems mostly upright and somewhat outwardly spreading giving a uniformly mounded appearance to the plant. Very freely branching, about five lateral branches develop after removal of terminal apex (pinching); dense and full plants. Moderately vigorous.

*Plant height.*—About 22 cm.

*Plant width.*—About 32 cm.

*Lateral branches.*—Length: About 17 cm. Diameter: About 4 mm. Internode length: About 1.3 cm. Strength: Very strong, flexible. Texture: Pubescent. Color: 144A.

*Foliage description.*—Arrangement: Alternate. Length: About 5 cm. Width: About 3.8 cm. Apex: Cuspidate to mucronate. Base: Attenuate to truncate. Margin: Palmately lobed, sinuses between lateral lobes mostly divergent, however, occasionally parallel or overlapping. Texture: Upper and lower surfaces with very fine pubescence; veins prominent on lower surface. Color: Young foliage upper surface: Darker than 147A; slightly glossy. Young foliage lower surface: 147B. Mature foliage upper surface: Slightly darker than 147A; glossy. Mature foliage lower surface: 147B. Venation upper surface: 147A to 147B. Venation lower surface: 147B. Petiole length: About 2.1 cm. Petiole diameter: About 2 mm. Petiole color: 147A to 147B. Durability of foliage to stresses: Very good; strong and durable plants.

Inflorescence description:

*Appearance.*—Decorative-type inflorescence form with elongated oblong-shaped ray florets. Inflorescences borne on terminals above foliage. Disk and ray florets arranged acropetally on a capitulum. Not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity.*—Inflorescences maintain good color and substance for at least three weeks in an interior environment.

*Quantity of inflorescences.*—Typically grown as a spray-type; very freely flowering with about nine inflorescences per lateral stem, about 45 inflorescences per plant.

*Inflorescence bud.*—Height: About 5 mm. Diameter: About 6 mm. Color: Darker than 143A.

*Inflorescence size.*—Diameter: About 3.1 cm. Depth (height): About 1.8 cm. Diameter of disc: About 5 mm. Receptacle diameter: About 3 mm.

*Ray florets.*—Shape: Elongated-oblong. Orientation: Mostly upright, about 50° from perpendicular to peduncle. Aspect: Straight and flat. Length: About 1.8 cm. Width: About 6 mm. Apex: Emarginate, mammilate or dentate. Base: Attenuate; short to medium corolla tube. Margin: Entire. Texture: Smooth, glabrous, satiny. Number of ray florets per inflorescence: About 75; about 6 or 7 rows. Color: When opening, upper surface: Very light yellow, 2D to 5D, to white, 155D. Center appears light cream-colored. When opening, lower surface: Mostly white, 155D, apices tipped with purple, 77A to 72A. Fully opened, upper surface: Mostly white, 155D, apices tipped with purple, 77A to 72A. Fully opened, lower surface: Mostly white, 155D, apices tipped with purple, 77A to 72A. Purple apices more faint than upper surface apices.

*Disc florets.*—Shape: Tubular, elongated. Apex: Five-pointed. Length: About 6 mm. Width: Apex, about 1.5 mm; base, about 1 mm. Number of disc florets per inflorescence: Less than 20. Color: Immature: 144A. Mature: Apex: 5A to 7A. Mid-section and base: White, 155D.

*Peduncles.*—Length: First peduncle: About 2.3 cm. Fourth peduncle: About 4.5 cm. Seventh peduncle: About 4.9 cm. Diameter: About 1.5 mm. Angle to vertical: About 45° from vertical. Strength: Strong, wiry, flexible. Color: 144A.

*Reproductive organs.*—Androecium: Present on disc florets only. Anther color: 9A. Pollen amount: Scarce. Pollen color: 12A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Frosted Yoelmira', as illustrated and described.

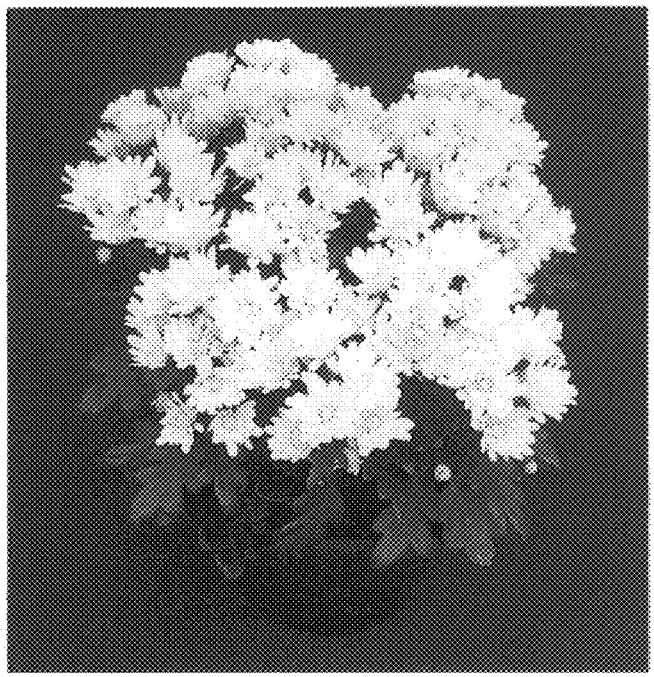
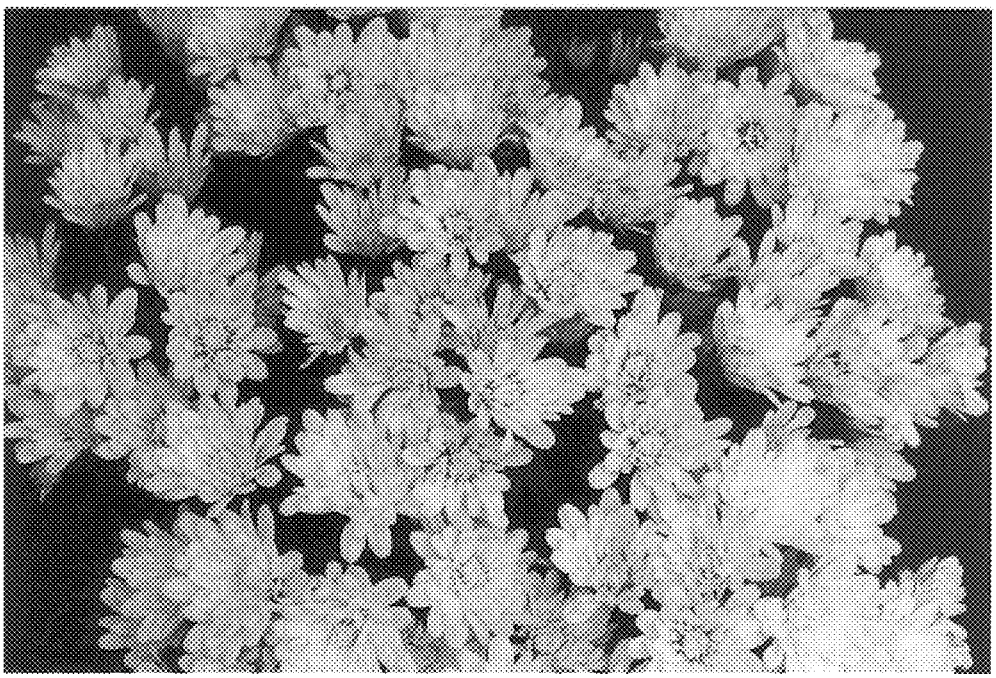

* * * * *